United States Patent [19]
Wardlaw et al.

[11] 4,027,660
[45] June 7, 1977

[54] MATERIAL LAYER VOLUME DETERMINATION

[76] Inventors: Stephen Clark Wardlaw, 16 Pine Orchard Road, Branford, Conn. 06405; Robert Aaron Levine, 31 Pilgrim Lane, Guilford, Conn. 06437; James Vincent Massey, III, 80 Driftwood Lane, Trumbull, Conn. 06610

[22] Filed: Apr. 2, 1976

[21] Appl. No.: 673,058

[52] U.S. Cl. .......................... 128/2 F; 73/425.4 P; 73/149; 128/DIG. 5; 128/2 G; 210/83; 210/DIG. 23

[51] Int. Cl.² .......................................... A61B 5/14

[58] Field of Search .............. 128/2 F, 2 G, DIG. 5; 73/149, 444, 425.4 P; 233/1 R, 26; 210/78, 83, DIG. 23, 24

[56] References Cited

UNITED STATES PATENTS

| 2,398,737 | 4/1946 | Elliot et al. | 73/425.4 P X |
|---|---|---|---|
| 3,437,266 | 4/1969 | Patterson | 210/78 X |
| 3,508,653 | 4/1970 | Coleman | 233/26 X |
| 3,513,976 | 5/1970 | James | 210/78 |
| 3,647,070 | 3/1972 | Adler | 210/83 |
| 3,898,982 | 8/1975 | Katsuda | 128/2 F |
| 3,920,557 | 11/1975 | Ayres | 128/2 F X |

FOREIGN PATENTS OR APPLICATIONS

| 2,243,569 | 3/1973 | Germany | 233/1 R |
|---|---|---|---|
| 1,391,053 | 4/1975 | United Kingdom | 128/2 G |

*Primary Examiner*—Kyle L. Howell
*Attorney, Agent, or Firm*—William W. Jones

[57] ABSTRACT

A technique for generally determining the volume of a layer of a constituent material in a centrifugally separated mixture of material. A centrifuge tube is used to hold the material mixture and an appropriately shaped body is disposed in the tube in the zone occupied by the constituent material whose volume is to be measured. The body reduces the available volume within the tube which may be occupied by the constituent material, and thus expands the axial extent of the constituent material to make visual measurement of the constituent material more accurate.

28 Claims, 11 Drawing Figures

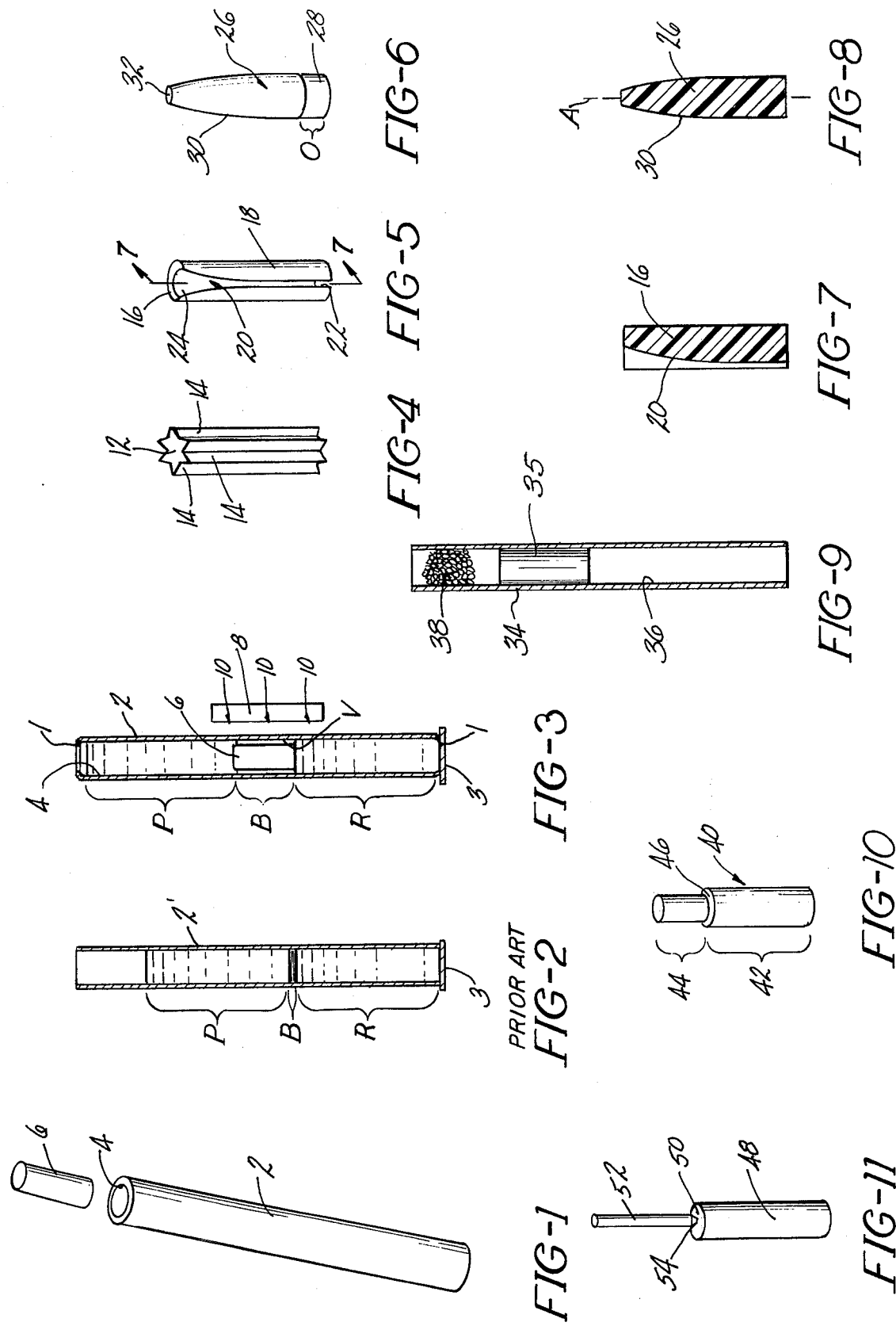

MATERIAL LAYER VOLUME DETERMINATION

This invention relates to a technique for enabling quick visual measurement of the approximate volume of a constituent material layer in a centrifuged material mixture. More particularly, this invention employs a body disposed in a centrifuge tube within the general confines of the layer to be measured and which acts to elongate the axial extent of the volume occupied by the layer to be measured.

Various techniques have been proposed for use in measuring the volume of a constituent layer of material within a material mixture, which material mixture has been centrifuged to separate out the various constituent materials into layers according to density, or specific gravity. These techniques have found particular application in measuring the several constituents of various biological fluids, such as blood, for example.

The particular blood constituent which has proven to be most difficult to quickly and easily measure is the buffy layer, which is made up of the various white cell types and platelets. In a centrifuged anticoagulated whole blood sample, the buffy layer is located between the red cell layer and the plasma layer, but because of the relative paucity of the buffy layer, a quick visual technique for measuring the buffy layer has, heretofore, been lacking.

One technique for determining the white cell count involves the use of a precisely measured volume of whole blood which is precisely diluted and placed in an optical counting chamber of a given volume. The diluted blood sample is then examined with a microscope and the leukocytes or white blood cells are visually counted. This technique is time consuming, requires relatively expensive equipment, and is subject to errors arising from inaccurate sample measurement and imprecise sample dilution.

Another technique has been devised for the automatic measurement of the leukocyte count of a blood sample. The sample of whole blood is manually or automatically diluted and the white cells are counted either by detecting and measuring light scatter from them in the sample as they pass through a confined space, or by measuring their effect on an electrical field as they pass through a small aperture. These automated techniques are quite accurate, but the equipment needed is quite expensive. The equipment also requires specially trained technicians to be used.

In the more general field of the volumetric measurement of constituent material layers in a centrifuged material mixture, it has been proposed to physically enlarge the axial extent of the layer of interest in order to perform some further operation on the layer. Specifically, it is proposed in the prior art to provide a specially formed flask for use in determining the leukocyte count in a whole blood sample. The flask is a centrifuge vessel and includes a mid-axial area of constricted internal diameter which, because of its reduced volume, will form a narrow vertical column of leukocytes. A high density material, such as mercury, must be used in this flask to raise the blood sample so as to ensure that the leukocytes occupy the narrow mid-axial neck of the vessel. Once properly positioned, the leukocytes are aspirated out of the vessel and subjected to further testing. It will be appreciated that such a flask is difficult to accurately form, is quite fragile, and cannot be readily used as a capillary tube due to the necessity of having one end closed to facilitate the introduction of the mercury thereinto. This flask thus is used for relatively large blood samples and the harvesting of leukocytes therefrom only.

Another proposal for centrifugal separation enhancement is set forth in the prior art. This latter technique involves the use of closely packed artificially produced microspheres which are diposed within a centrifuge tube to restrict the free volume available to be occupied within the tube by the centrifuged fluid material. The microspheres are formed with a plastic core having a metallic coating for accurately controlling the overall sphere density. Sphere densities, in turn, are selected so that a plurality of spheres will float in each layer of the centrifuged materials. Thus each material layer will have its particular density equal to the density of an associated plurality of spheres, which spheres, by reason of the density gradiant of the centrifuged mixture, will be restricted to and "float in" the particular material layer of the same density. In this manner the axial extent of each layer will be expanded for easier visual measurement. The spheres of different densities can also be of different colors to further contrast the several layers each from the others. This technique has several problems one of which relates to centrifugation in general, i.e. the problem of how to get the spheres into the tube, especially if the tube is of capillary size, and the other of which relates to its use in a buffy layer measuring technique. This latter problem arises from the packing characteristics of spheres wherein the resultant free space available to be occupied by the buffy layer is about 33% of the original free space present without the spheres. This means that the axial extent of the buffy layer in a centrifuged blood sample can only be increased about threefold using microspheres alone, and this degree of increase is insufficient to permit simple, visual measurement of the volume of the buffy layer with any acceptable degree of accuracy.

In order to provide a quick, inexpensive visual technique for determining the general buffy layer measurement or leukocyte count in an anticoagulated blood sample, we propose the use of at least one axially elongated volume-occupying mass which is made of a material having a specific gravity such that the mass will float upon, or slightly in the red cell layer of the centrifuged blood sample. The mass is disposed in the capillary tube bore, has its axis of elongation substantially coincidental with the tube bore axis and combines with the tube bore to form an axially extending free space between the tube bore wall and the exterior of the mass. The volume of the free space is substantially less than the free volume of the tube bore so that the axial extent of the buffy layer will be markedly increased when the buffer layer is positioned in the free space during and after centrifugation.

The geometric form of the mass can vary widely, as will be outlined in greater detail hereinafter. The mass can also be used in combination with a microsphere cluster for further enhancement. Furthermore, the mass can be used for visual identification of the several internal constituents of the buffy layer, as will be outlined hereinafter.

It is, therefore, an object of this invention to provide a technique for use in visually determining the general leukocyte and platelet count which make up the buffy layer in a sample of whole blood.

It is a further object of this invention to provide a technique of the character described which entails the use of a capillary-type centrifuge tube containing an axially elongated volume-occupying mass selectively positioned in the buffy layer and floating on the red cell layer of the blood sample.

It is yet another object of this invention to provide a technique of the character described which utilizes expendable paraphenalia and can be performed quickly in a doctor's office by relatively untrained personnel.

It is yet another object of this invention to provide a technique of the character described for performing a differential white cell and platelet count.

It is an additional object of this invention to provide a technique of the character described which is relatively accurate, and inexpensive to use.

These and other objects and advantages of the invention will become more readily apparent from the following detailed description of several embodiments of the invention taken in conjunction with the accompanying drawings, in which:

FIG. 1 is an exploded perspective view of one embodiment of an apparatus usable in determining the leukocyte or white cell and platelet count in accordance with the invention;

FIG. 2 is an axial sectional view of a capillary tube employed in accordance with prior art teachings for centrifugation of whole blood sample into its constituent components, i.e. red cells, white cells, platelets and plasma;

FIG. 3 is an axial sectional view of the apparatus of FIG. 1 as it is employed to make a visual measurement of the white cell and platelet count in a centrifuged whole blood sample;

FIGS. 4–6 are perspective views of several variations of the insert portion of the apparatus of FIG. 1;

FIG. 7 is an axial sectional view of the modified insert of FIG. 5 taken along line 7—7 thereof;

FIG. 8 is an axial sectional view of the modified insert of FIG. 6;

FIG. 9 is an axial sectional view of a specimen tube showing an embodiment of the invention which includes interphase-demarcating microspheres of particulate material of appropriate specific gravities used in conjunction with an axially elongated volume-occupying body of the type shown in FIG. 1; and FIGS. 10 and 11 are perspective views of further embodiments of an insert which may be used as the volume-occupying mass in this invention.

Referring now to the drawings, there is shown in FIG. 1 one embodiment of an apparatus which can be used in accordance with the invention for making a visual determination of the approximate white cell and platelet count in a sample of whole blood. The apparatus includes a capillary tube 2 of conventional construction having a through bore 4 which is open at both ends of the tube 2. An axially elongated volume-occupying mass 6 is positioned inside of the tube bore 4. In the embodiment shown in FIG. 1, the mass 6 takes the form of a right cylindrical insert or plug which is composed of a material having a predetermined specific gravity which renders the mass buoyant upon the centrifuged red cell mass. Due to its shape, the insert 6 will be held in the tube bore 4 so that both have substantially coincidental axes at all times. The diameter of the insert 6 is sufficiently smaller than the diameter of the tube bore 4 so as to be slidable within the tube bore 4 so that the insert 6 can gravitate to the red cell layer during centrifugation of the blood sample and float upon the red cell layer after centrifugation.

The difference between the respective diameters of the insert 6 and tube bore 4 will form a free space of restricted volume, which free space is occupied by the centrifuged layer of white cells and platelets. By restricting the size of the free space available to the buffy layer, the apparent height or thickness of the buffy layer will be expanded over that obtained in an unrestricted capillary tube bore. Changes in the volume of the buffy layer from sample to sample will thus be "magnified" so that one can visually determined whether the white cell and platelet count is high, low, or average, generally speaking. This general determination will then be used to indicate whether further more sophisticated tests are needed. It will be appreciated that the degree of expansion of the height of the buffy layer can be varied by varying the difference between the diameters of the insert 6 and tube bore 4. Expansion factors in the range of four up to twenty may be obtained. For example, an expansion factor or multiple of nine is readily obtained. It will be appreciated that this apparent expansion of the buffy layer is the result of the fact that the insert 6 occupies volume within the tube adjacent to the red cell layer, and thus reduces the free volume available to the buffy layer by a multiple of 0.75 or more.

FIG. 2 illustrates a capillary tube 4 containing a blood sample which has been centrifuged down to its constituent component layers. It will be noted that the lower end of the tube bore has been sealed by a dab of clay, wax, or the like 3 prior to centrifugation. The red cell layer is denoted generally by the letter R, the white cell and platelet layer e.g. the buffy layer, by the letter B, and the plasma layer by the letter P. It will be noted that the axial extent or thickness of the white cell and platelet layer B is diminimus thus making it impossible to visually determine generally whether the white cell and platelet count is abnormally high, low, or average.

Referring now to FIG. 3, there is shown the apparatus of FIG. 1 used to axially elongate the bounds of the buffy layer B. The sample has been centrifuged in the tube 2 with the volume-occupying mass insert 6 in place within the tube bore 4. As can be noted from FIG. 3 and as previously described, the tube bore 4 and the side surface of the insert 6 combine to form an annular free volume V directly above the red cell layer R into which annular free volume the buffy layer settles during centrifugation. It will also be noted that the annular free volume V is substantially smaller than a corresponding free volume within the tube bore, and thus the axial extent of the buffy layer occupying the annular free volume is substantially expanded. In other words, the distance between the upper and lower menisci of the buffy layer is increased over that shown in FIG. 2. A minimum expansion multiple of about four is considered to be useful in visual white cell and platelet count determination in accordance with this invention. If so desired, a reference guide 8 may be used for comparison with the apparatus for determining high, low, or average white blood cell and platelet count. The guide 8 may display reference indicia 10 for alignment with the upper and lower menisci of the buffy layer. Thus a measurement of the distance between the upper and lower menisci of the buffy layer is made to determine the white cell and platelet counts. More precise measurements of the relative axial expansion of the buffy layer by the use of mechanical, optical or electrical means can also be made from the apparatus of FIG. 3.

The apparatus of FIGS. 1 and 3 is used as follows. The insert 6 is positioned inside of the tube bore 4 and the ends of the tube 2 may be inwardly crimped as at 1 to retain the insert within the bore, or the insert may be adhered to the wall of the tube bore by means of a blood-soluble adhesive such as gum acacia. The tube is then used in a conventional manner to draw a blood sample from a patient by means of a finger prick or the like. The drawn sample is then centrifuged with the resultant separation and elongation of the buffy layer as shown in FIG. 3.

It will be noted that the axially elongated shape of the insert 5 lends itself to formation thereof by extrusion of a synthetic resinous melt and subsequent cutting of the extrudate to length. The insert may also be made by injection molding of a resinous melt. The insert 6 is made of a material or materials having a specific gravity or cross-sectional bulk density in the range of 1.02 gm/cc to 1.09 gm/cc, and preferably about 1.04 gm/cc so that the insert 6 will be buoyant upon the red cell layer and yet sink through the buffy layer. Examples of such a material are acrylonitrile butadiene styrene (ABS), "commercial" styrene, and MMA styrene copolymer. A layering of different density materials may also be used to form the insert so long as the cross-sectional bulk density of the layered insert is an appropriate value.

The shape of the insert 6 shown in FIGS. 1 and 3 is right cylindrical, however FIGS. 4, 5, 6 and 10 disclose other insert configurations which can be used without departing from the spirit of the invention.

FIG. 4 discloses an insert 12 which is provided with one or more axial channels 14 formed in its side surface. The channels 14 form passages in which the buffy layer will settle during centrifugation.

FIG. 5 discloses an insert 16 which has a cylindrical side wall 18. An axial channel 20 into which the buffy layer settles is formed in the side wall. The channel 20 has a restricted mouth 22 at its lower end which is adjacent to the red cell layer, and the volume of the channel 20 expands at a logarithmic rate from the mouth 22 to its upper end 24. The use of a logarithmic or other non-linear rate of expansion of the channel 20 can provide an accurate means for determining the white cell and platelet count when a wide range of variation is expected, as in the case of abnormally low or abnormally high counts. FIG. 7 shows the logarithmic slope of the wall of the channel 20 in the insert 16.

FIG. 6 discloses an insert 26 which has a lower end 28 adjacent to or in the red cell layer and which may be formed with a cylindrical side wall for a short distance D. The side wall 30 of the insert 26 then slopes upwardly and inwardly toward the axis of the insert 26 at a logrithmetic or other non-linear rate up to the top end 32 of the insert. FIG. 8 illustrates the logrithmetic rate of slope of the side wall 30 toward the axis A. This configuration also permits increased accuracy over a wide range by logrithmetically or non-linearly increasing the size of the free volume between the insert side wall and the tube bore wall in which the buffy layer is disposed.

It has also been found that a distinctly colored material such as dyed particles of styrene having specific gravities of about 1.035 and 1.075 gm/cc may be added to the blood sample and used in conjunction with the axially elongated insert to sharply define the menisci between the platelet layer and the white cell lymphocyte layer, and between the lymphocyte layer and the polymorphonuclear-leukocyte (polys) layer. This internal sharp definition within the buffy layer further aids in reading the white cell and platelet count in accordance with this invention.

FIG. 9 discloses such an embodiment wherein the styrene particles 38 are adhered to the internal bore wall 36 of a capillary tube 34 by means of an adhesive such as gum acacia soluble in blood and the axially elongated insert 35 is likewise adhered to the bore wall 36.

Referring now to FIG. 10, there is shown an insert 40 which is generally cylindrical in shape, but which has at least two adjacent zones with different diameters. The lowermost zone 42 has a larger diameter which will provide a greater buffy layer elongation multiple, for example multiple of about twenty, and the uppermost zone 44 has a smaller diameter which will provide a lesser buffy layer elongation multiple, for example a multiple of about three. The two zones 42 and 44 are bridged by a radial shoulder 46. This insert will provide multiple linear expansion factors for the buffy layer, and can be used to quickly indicate an abnormally high white cell and platelet count. This high count will be observed when the buffy layer is expanded above the shoulder 46. The second zone 44 will then give a quick indication of how much too high the count is.

Referring to FIG. 11, there is shown an insert 48 which is generally cylindrical in shape and has integral with its upper end 50 an elongated handle 52. This handle can aid in packing the inserts in the capillary tubes and will protrude from the ends of the capillary tubes. The handle 52 can thus be manually grasped after the blood sample is drawn into the capillary tube and pumped up and down slowly to cause any dyes in the tube to mix with the blood. The handle 52 can be connected to the insert 48 at a weakened area 54 so that the handle 52 can be snapped off of the insert after mixing but prior to centrifugation.

In order to even further elongate the white cell layer, one could provide a coating of microspheres on the external surface of the insert or in any channels formed therein. The microspheres can be adhered to each other and to the insert by means of a soluble adhesive, such as gum acacia which will dissolve in blood. In the event that some fluid other than blood is being tested, the particular adhesive utilized will, of course, be one that is soluble in the fluid being tested.

As previously noted, with the use of an axially elongated volume-occupying mass in the tube bore, axial elongation of the layer being measured can be increased by a multiple in the range of four to about twenty. When determining white cell and platelet count in a blood sample, the preferred range of axial elongation of the white cell layer is a multiple in the range of about five to about fifteen.

It has been discovered that when an axial elongation of the buffy layer is produced within the preferred range, the layering by specific gravity of the individual components of the buffy layer, e.g. the polymorphonuclears, the mononuclear cells including lymphocytes, monocytes, and platelets. The buffy layer components will layer as follows in order of lessening specific gravity, the polys, then the monos and lymphocytes (in the same layer), and lastly the platelets.

As previously noted, when the volume-occupying insert is formed from a material of the proper specific gravity and has an appropriate axial dimension, the insert will settle slightly into the upper portion of the red cell layer of the centrifuged blood sample. It is in this portion of the red cell layer that the reticulocytes, or immature red cells, layer out during centrifugation. Thus the insert will cause axial elongation of the reticulocyte sub-layer of the red cell layer. It has been discovered that an approximate reticulocyte count can also be made with the addition of a fluorescent stain to the blood sample. This count is useful to the physician in determining the rate of production of new red blood cells by a patient.

To observe this internal layering of the buffy layer, and the reticulocyte layer a fluorescent stain, such as Acridine orange, or the like, is added to the sample prior to centrifugation. The stain will be absorbed to varying degrees by the different constituents of the buffy layer, and by the reticulocytes and thus when exposed to fluorescent light, the various layers will fluoresce to different degrees. Thus the thickness of each sub-layer within the buffy layer and the thickness of the reticulocyte layer can be observed by illuminating the tube with light of the proper wavelength. If desired, optical magnification may be used to observe this layering. The stain may be coated on the tube bore wall, may be coated on the insert, or may be inserted into the tube bore in the form of a self sustaining, but soluble mass. For use with non-anticoagulated blood, an anticoagulant such as heparin can be added in the same manner to the blood sample. It will thus be appreciated that this invention makes possible a quick, simple visual diffential white cell and platelet count and a reticulocyte count through the use of an appropriate fluorescent stain additive and a suitable light source, both of which may be readily available in a doctor's office.

An apparatus formed in accordance with this invention which will provide a nine fold axial expansion of the distance between the upper and lower menisci of the buffy layer in a sample of centrifuged whole blood includes a capillary centrifuge tube having an internal bore diameter of 0.05575 in. The volume-occupying mass is a right cylinder made from Rexolite, which is a cross-linked styrene having a specific gravity of 1.043 gm/cc, and having a diameter of 0.053 in. and a height of about ½ in.

It will be appreciated by those skilled in the art that this invention will enable visual or mechanical determination of the white cell and platelet count in a centrifuged sample of whole blood to be made at a low cost and quickly. With proper buffy layer expansion, a differential white cell and platelet determination can be made by using the apparatus and method of this invention. The apparatus of this invention is such that it can be prepackaged and can take the form of inexpensive disposable paraphenalia. Expensive and time consuming cell counters are not required to practice the technique of this invention.

Since many changes and variations of the disclosed embodiments of the invention may be made without departing from the inventive concept, it is not intended to limit the invention otherwise than as required by the appended claims.

What is claimed is:

1. For use in measuring the approximate volume of a constituent material layer in a centrifuged material mixture having at least first and second adjacent material layers of different densities, an apparatus comprising: a tube the bore of which is of substantially constant diameter for containing the centrifuged material mixture; and a volume-occupying mass disposed within the bore in said tube, said mass comprising an axially elongated body formed of a resinous material which sinks through the layer of lesser density but is buoyant upon the layer of greater density, said body having an outside diameter which is sufficiently smaller than the tube bore diameter to form a free space means between said body and said tube bore operable to reduce the available free volume within said tube which substantially all of the layer of lesser density will occupy to axially expand the extent of the layer of lesser density by a multiple of at least about four.

2. The apparatus of claim 1, wherein said tube is a capillary tube open at both ends for drawing by capillary action a sample of the material mixture.

3. The apparatus of claim 2, wherein the ends of said capillary tube are inwardly crimped to retain said mass in said tube.

4. The apparatus of claim 1, wherein said body is a generally cylindrical body having its axis substantially coincidental with the axis of said tube.

5. The apparatus of claim 4, wherein said cylindrical body includes at least one axially extending groove in its outer side surface which the layer of lesser density occupies.

6. The apparatus of claim 1, wherein said body has an outer side surface shaped to form means for providing non-linear axial expansion of the layer of lesser density.

7. The apparatus of claim 1, wherein said body has an outer side surface shaped to form means for providing multiphase linear axial expansion of the layer of lesser density.

8. The apparatus of claim 1, further comprising colored particulate material of different densities and secured in a cluster to an inner surface of said tube by means of an adhesive material which is soluble in the material being measured, said particulate material being operable to settle into particular interphases between adjacent layers of different density to sharply demarcate the interphases.

9. For use in measuring the approximate white cell and platelet count in a centrifuged sample of whole anti-coagulated blood, an apparatus comprising: a transparent tube for containing the centrifuged blood sample; at least one volume-occupying body formed from a material having a specific gravity in the range of about 1.02 to about 1.09 gm/cc and disposed in said tube, said body being elongated along an axis which is substantially coincidental with the tube axis, said body being buoyant upon the red cell layer of the centrifuged blood sample, and said body being sufficiently movable within the tube so as to settle onto the red cell layer during centrifugation, said body being radially sized so as to form completely externally of said body a constricted free volume means adjacent to an inner surface of said tube and visible therethrough which constricted free volume means is operative to receive and axially elongate, by a multiple of at least about four, the extent of substantially all of the white cell and platelet layer.

10. The apparatus of claim 9, wherein said tube is a capillary tube open at both ends for drawing a blood sample.

11. The apparatus of claim 10, wherein the ends of said capillary tube are radially inwardly crimped to retain said body in said tube.

12. The apparatus of claim 10, wherein said body is a generally cylindrical body.

13. The apparatus of claim 12, wherein said cylindrical body has at least one axially extending groove in its side wall forming at least a part of said free volume means.

14. The appartus of claim 10, wherein said body has a side surface shaped to form a free volume means operative to provide non-linear axial elongation of the extent of the white cell and platelet layer.

15. The apparatus of claim 10, wherein said body has a side surface shaped to form a free volume means operative to provide multi-phase linear axial elongation of the extent of the white cell and platelet layer.

16. The apparatus of claim 10, wherein said free volume means is operative to provide axial elongation of the white cell and platelet layer of a multiple in the range of about five to about fifteen and further comprising a stain in said tube which is selectively absorbed by the white cell component cells and the platelets to provide a differential buffy layer count.

17. The apparatus of claim 16, further comprising colored particulate material of at least two distinctly different densities, said particulate material being adhered together and adhered to a surface within said tube by an adhesive which is soluble in blood, and said particulate material providing means for demarcating at least two different interphases between adjacent sub-component layers in the buffy layer.

18. For use in measuring the approximate white cell and platelet count in the buffy layer of a centrifuged sample of anticoagulated whole blood, an apparatus comprising a transparent capillary tube for containing the centrifuged blood sample; and volume-occupying means formed from a material having a specific gravity in the range of about 1.02 to about 1.09 gm/cc and disposed in said tube and buoyant upon the red cell constituent of the centrifuged sample for forming a free volume means which is visible through the tube and which is adjacent to the red cell constituent for receiving substantially all of the buffy layer constituent and for axially elongating the distance between the upper and lower menisci of the buffy layer by a multiple of at least abour four.

19. The apparatus of claim 18, wherein said volume-occupying means is a generally cylindrical body having its axis substantially coincidental with the tube axis.

20. The apparatus of claim 18 wherein said free volume means is operative to elongate said distance by a multiple in the range of about five to about fifteen.

21. The apparatus of claim 20, further comprising a stain in said tube which is selectively absorbed to different degrees by the different cell types in the buffy layer to provide for a differential buffy layer count.

22. The apparatus of claim 21, further comprising colored particulate material of at least two distinctly different densities adhered to a surface within said tube by an adhesive which is soluble in blood, said particulate material providing means for demarcating at least two different interphases between adjacent layers of different cell types in the buffy layer.

23. For use in measuring the approximate white cell and platelet count in a centrifuged sample of anticoagulated whole blood, an apparatus comprising a capillary tube for containing the centrifuged blood sample; and volume-occupying means formed from a material having a specific gravity in the range of about 1.02 to about 1.09 gm/cc and disposed in said tube and buoyant upon the red cell layer of the centrifuged sample, said volume-occupying means being operable to reduce the free volume within the tube available for containment of substantially all of the white cell and platelet layer by a multiple of at least about 0.75.

24. For use in measuring the approximate white cell and platelet count in a centrifuged sample of anticoagulated whole blood, an apparatus comprising: a transparent capillary tube for receiving and containing the sample of blood to be centrifuged; a volume-occupying mass disposed within said capillary tube and forming with the bore thereof a free space means which is visible through the tube and is operable to receive and axially elongate substantially all of the white cell and platelet layer of the blood sample by a multiple of at least about four, aid volume-occupying mass being formed of a material which has a specific gravity in the range of about 1.02 to about 1.09 gm/cc and is buoyant upon the red cell layer of the blood sample after centrifugation thereof; and an adhesive material securing said volume-occupying mass to an inner surface of the tube, said adhesive material being soluble in blood.

25. For use in measuring the approximate differential white cell and platelet count in the buffy layer in a centrifuged sample of anticoagulate whole blood, an apparatus comprising: a capillary tube for drawing and containing the sample of blood to be centrifuged; an axially elongated body disposed in said tube to occupy space therein normally available to the buffy layer, said body being formed of a material which has a specific gravity in the range of about 1.02 to about 1.09 gm/cc and is buoyant upon the red cell layer of the centrifuged blood sample, said body combining with said tube to form a free space means in which substantially all of the buffy layer is disposed with said free space means being operable to elongate the axial extent of the buffy layer by a multiple in the range of about five to about fifteen; and a stain in said tube which stain is absorbed to differing degrees by the several constituent white cell types and the platelets to form within the buffy layer, sub-layers of white cell types and platelets distinguishable by differential coloring.

26. The apparatus of claim 25, wherein said body includes a handle part protruding from an open end of said tube for manual manipulation in an axial direction to mix the blood and stain prior to centrifugation.

27. The apparatus of claim 25, further comprising colored particulate material of at least two distinctly different densities adhered to a surface within said tube by an adhesive which is soluble in blood, said particulate material providing means for demarcating at least two different interphases between adjacent sub-layers within the buffy layer.

28. For use in measuring the approximate reticulocyte count in a centrifuged sample of anticoagulated whole blood, an apparatus comprising: a capillary tube for drawing and containing the blood sample to be centrifuged; an axially elongated body disposed in said tube, said body being formed of a material having a specific gravity in the range of about 1.02 to about 1.09 gm/cc which will cause the body to settle into and float in the red cell layer to an extent sufficient to displace enough of the volume in the tube normally occupied by the reticulocyte layer to form a free space means within the tube operative to receive and axially elongate substantially all of the reticulocyte layer by a multiple in the range of about five to about fifteen; and a stain in said tube which is absorbed by the reticulocyte layer to cause differential coloration thereof.

* * * * *

UNITED STATES PATENT OFFICE
CERTIFICATE OF CORRECTION

Patent No. 4,027,660           Dated June 7, 1977

Inventor(s) S. C. Wardlaw, R. A. Levine & J. V. Massey

It is certified that error appears in the above-identified patent and that said Letters Patent are hereby corrected as shown below:

Column 5, line 15      change "5" to --6--;

Column 10, line 24     change "anticoagulate" to --anticoagulated--.

Signed and Sealed this twenty-third Day of August 1977

[SEAL]

Attest:

RUTH C. MASON
Attesting Officer

C. MARSHALL DANN
Commissioner of Patents and Trademarks

UNITED STATES PATENT OFFICE
CERTIFICATE OF CORRECTION

Patent No. 4,027,660            Dated June 7, 1977

Inventor(s) S. C. Wardlaw, R. A. Levine and J. V. Massey, III

It is certified that error appears in the above-identified patent and that said Letters Patent are hereby corrected as shown below:

In column 5, line 20, "or cross-sectional bulk density" should be deleted.

In column 5, line 21, "gm/cc" should be deleted, each occurrence.

In column 5, line 66, "gm/cc" should be deleted.

In column 7, line 45, "gm/cc" should be deleted.

In Claim 9, line 7, "gm/cc" should be deleted.

In Claim 18, line 7, "gm/cc" should be deleted.

In Claim 23, line 7, "gm/cc" should be deleted.

In Claim 24, line 13, "gm/cc" should be deleted.

In Claim 25, line 9, "gm/cc" should be deleted.

In Claim 28, line 8, "gm/cc" should be deleted.

*Signed and Sealed this*

*Twenty-eighth* Day of *February 1978*

[SEAL]

Attest:

RUTH C. MASON      LUTRELLE F. PARKER
*Attesting Officer*      *Acting Commissioner of Patents and Trademark*